United States Patent
Just et al.

(10) Patent No.: US 10,874,832 B2
(45) Date of Patent: Dec. 29, 2020

(54) DEFLECTABLE CATHETER SHAFT

(71) Applicant: St. Jude Medical, Cardiology Division, Inc., St. Paul, MN (US)

(72) Inventors: Dale E. Just, Minneapolis, MN (US); Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 175 days.

(21) Appl. No.: 16/077,566

(22) PCT Filed: Feb. 9, 2017

(86) PCT No.: PCT/US2017/017118
§ 371 (c)(1),
(2) Date: Aug. 13, 2018

(87) PCT Pub. No.: WO2017/142778
PCT Pub. Date: Aug. 24, 2017

(65) Prior Publication Data
US 2019/0030287 A1 Jan. 31, 2019

Related U.S. Application Data

(60) Provisional application No. 62/295,352, filed on Feb. 15, 2016.

(51) Int. Cl.
*A61M 25/01* (2006.01)
*A61B 1/005* (2006.01)
(Continued)

(52) U.S. Cl.
CPC ......... *A61M 25/0147* (2013.01); *A61B 1/008* (2013.01); *A61B 1/0055* (2013.01);
(Continued)

(58) Field of Classification Search
CPC ... A61B 1/0055; A61B 1/0056; A61B 1/0057; A61B 1/008; A61M 25/0147; A61M 25/0138; A61M 2025/0161
(Continued)

(56) References Cited

U.S. PATENT DOCUMENTS

| 2006/0200000 A1* | 9/2006 | Sato | A61B 1/0055 |
| | | | 600/146 |
| 2012/0029334 A1* | 2/2012 | Tegg | A61M 25/007 |
| | | | 600/373 |
| 2014/0135685 A1* | 5/2014 | Kabe | A61M 25/0138 |
| | | | 604/95.04 |

FOREIGN PATENT DOCUMENTS

| EP | 1681013 A1 | 7/2006 |
| JP | 2009112537 A | 5/2009 |

\* cited by examiner

*Primary Examiner* — Deanna K Hall
(74) *Attorney, Agent, or Firm* — Dykema Gossett PLLC

(57) ABSTRACT

Embodiments include a catheter shaft (12) having an elongated structure with a distal portion (18) and proximal portion (16). The distal portion (18) can include a distal tip (36), a proximal connector (38), and a plurality of pivoting hollow cylindrical segments (40) disposed between the proximal connector (38) and distal tip (36) along a longitudinal axis extending through the elongated structure. A plurality of connections (42, 44) can be disposed along diametrically opposed sides of the distal portion (18) and configured to connect the distal tip (36), the pivoting hollow cylindrical segments (40), and the proximal connector (38). A diametrically opposed pair of tabs (54-1, 54-2) can extend from an inner wall of each of the pivoting hollow cylindrical segments (40) to form first and second pullwire tunnels (81-1, 81-2). First and second pullwires (52-1, 52-2) can extend through the first and second pullwire tunnels (81-1, 81-2).

23 Claims, 7 Drawing Sheets

(51) Int. Cl.
*A61B 1/008* (2006.01)
*A61B 8/08* (2006.01)
*A61B 8/00* (2006.01)
*A61B 8/12* (2006.01)

(52) U.S. Cl.
CPC .......... *A61B 1/0056* (2013.01); *A61B 1/0057* (2013.01); *A61B 8/0883* (2013.01); *A61B 8/12* (2013.01); *A61B 8/445* (2013.01)

(58) Field of Classification Search
USPC ........................................................ 604/528
See application file for complete search history.

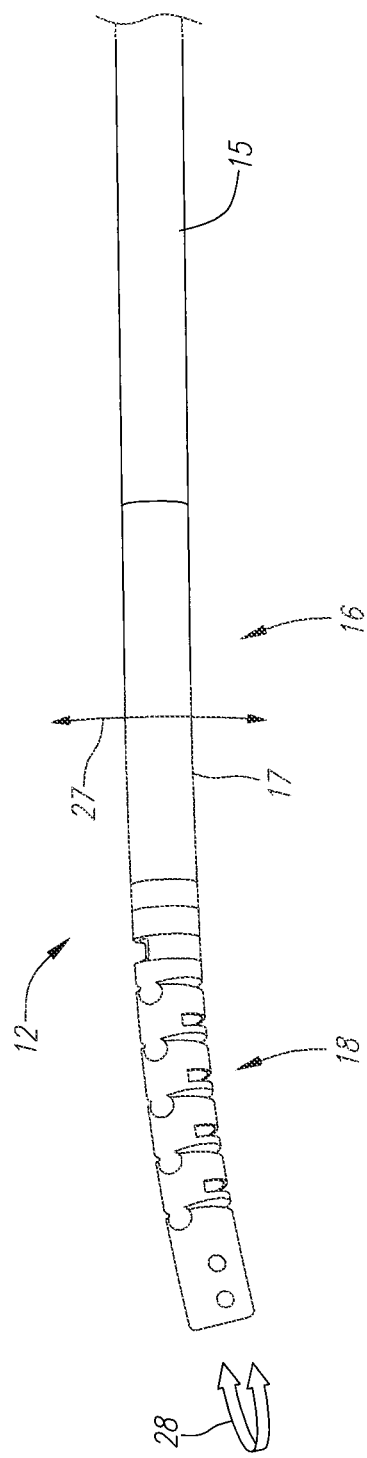
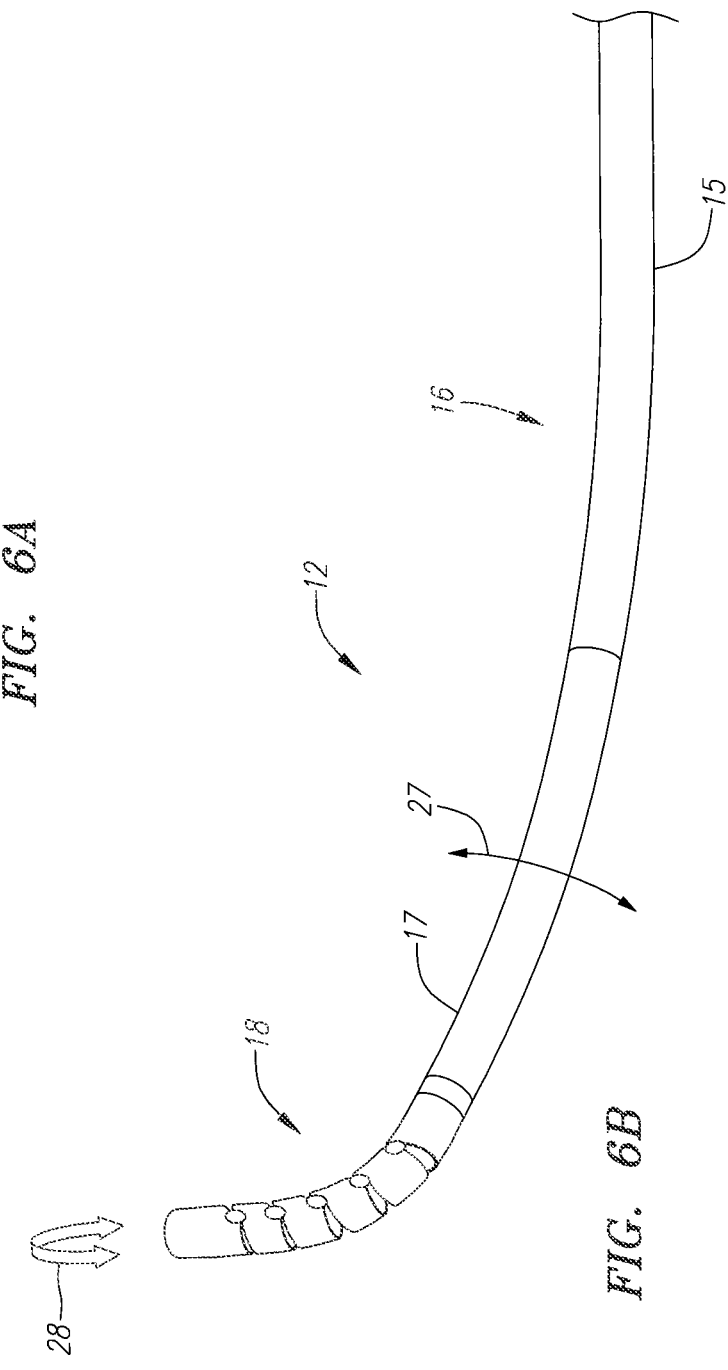

DEFLECTABLE CATHETER SHAFT

CROSS-REFERENCE TO RELATED APPLICATION

This application claims the benefit of U.S. provisional application No. 62/295,352, filed 15 Feb. 2016, which is hereby incorporated by reference as though fully set forth herein.

BACKGROUND a. Field

The present disclosure relates generally to a deflectable catheter shaft.

b. Background

Some medical procedures can involve accessing areas of the heart to perform diagnostic, therapeutic, and/or mapping procedures. Medical devices, such as catheters have been used for medical procedures for a number of years. It is necessary for catheters to exhibit a degree of flexibility to be able to maneuver through the vasculature of a patient during the performance of cardiac procedures and a degree of steering to position a distal end of the catheter in a particular location within the heart. For example, a catheter can be equipped with an ultrasound transducer located at a distal end of the catheter. The ultrasound transducer can be introduced into the heart and the catheter can be deflected to position the ultrasound transducer in a particular position and/or orientation, allowing for visualization of cardiac structures and/blood flow within the heart, for example.

A catheter can also be equipped with a therapeutic device and/or mapping device at a distal end of the catheter. The therapeutic device can include an ablation device and the mapping device can include a magnetic coil and/or an electrode, for example. The therapeutic device and/or a mapping device can be introduced into the heart via the catheter and the catheter can be deflected to position and/or orient the therapeutic device and/or mapping device.

BRIEF SUMMARY

Various embodiments herein provide a deflectable catheter shaft. In at least one embodiment, a catheter shaft can comprise an elongated structure that includes a distal portion and a proximal portion. The distal portion can include a distal tip, a proximal connector, and a plurality of pivoting hollow cylindrical segments disposed between the proximal connector and the distal tip along a longitudinal axis that extends through the elongated structure. The catheter shaft can include a plurality of connections disposed along diametrically opposed sides of the distal portion that are configured to connect the distal tip, the plurality of pivoting hollow cylindrical segments, and the proximal connector. The catheter shaft can include a diametrically opposed pair of tabs that extend from an inner wall of each of the plurality of pivoting hollow cylindrical segments that forms a first and second pullwire tunnel. The catheter shaft can include a first and second pullwire that extend through the first and second pullwire tunnel.

In at least one embodiment, a catheter shaft can comprise an elongated structure, wherein the elongated structure includes a distal portion and a proximal portion. The distal portion can include a proximal hollow cylindrical segment disposed next to and connected with a pivoting hollow cylindrical segment. The proximal hollow cylindrical segment can include a distal face and the pivoting hollow cylindrical segment can include a proximal face. A first and second longitudinally extending projection can be disposed on at least a first one of the distal face of the proximal hollow cylindrical segment and the proximal face of the pivoting hollow cylindrical segment. A first and second socket corresponding to the first and second longitudinally extending projections can be disposed on at least a second one of the distal face of the proximal hollow cylindrical segment and the proximal face of the pivoting hollow cylindrical segment. A diametrically opposed pair of tabs can extend from an inner wall of each hollow cylindrical segment.

In at least one embodiment, a catheter shaft can comprise an elongated structure. The elongated structure can include a distal portion that includes a distal tip and a proximal portion connected to the distal portion. The distal portion can include a plurality of hollow cylindrical segments that are connected to one another via diametrically opposed hinges. Each of the plurality of hollow cylindrical segments includes a diametrically opposed pair of tabs that extend from an inner wall of each hollow cylindrical segment to form first and second diametrically opposed pullwire tunnels. A first pullwire can extend from the proximal portion through the first pullwire tunnel and can be connected to the distal tip. Pulling of the first pullwire can cause the distal tip to deflect in a first direction. A second pullwire can extend from the proximal portion through the second pullwire tunnel and can be connected to the distal tip. Pulling of the second pullwire can cause the distal tip to deflect in a second direction.

BRIEF DESCRIPTION OF THE DRAWINGS

FIG. 6A is a side view of a catheter shaft in a first flexed state, in accordance with embodiments of the present disclosure.

FIG. 6B is a side view of the catheter shaft in FIG. 6A in a second flexed state, in accordance with embodiments of the present disclosure.

DETAILED DESCRIPTION OF THE INVENTION

Figure 1:
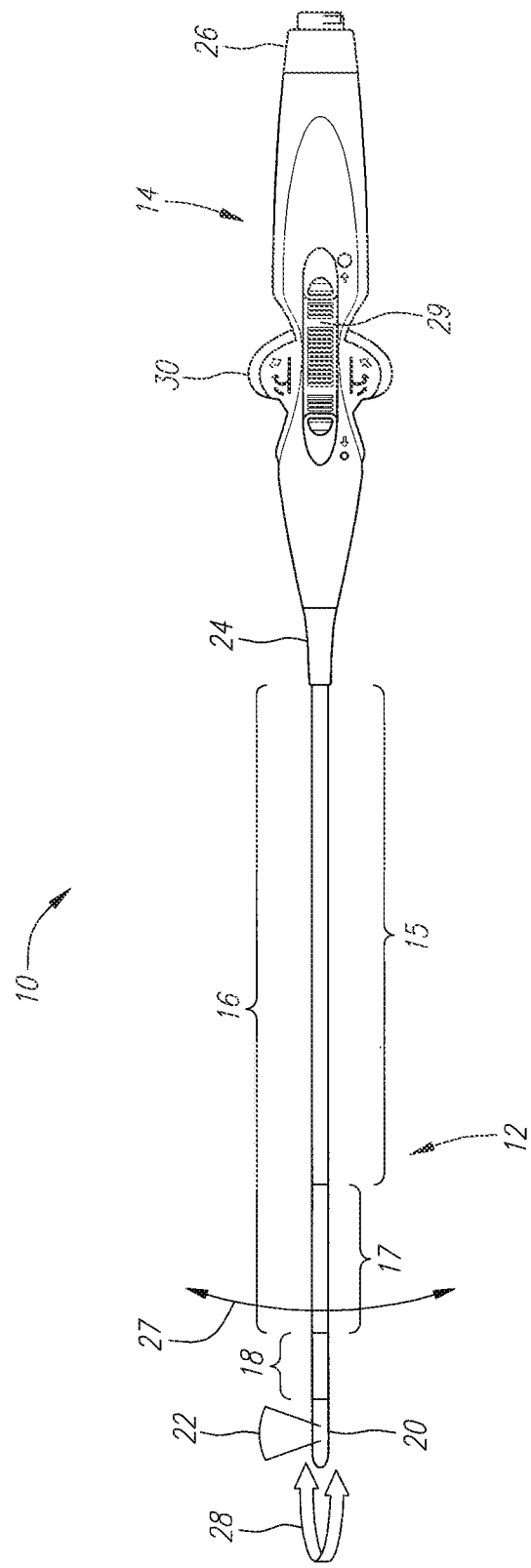
FIG. 1 is a side view of a catheter that includes a catheter shaft, in an undeflected state, connected to a catheter handle, in accordance with embodiments of the present disclosure.

Referring now to the drawings wherein like reference numerals are used to identify identical or similar components in the various views, FIG. 1 is a side view of a medical device 10 that includes a catheter shaft 12, a proximal end of which is connected to a handle assembly 14. The catheter shaft 12 is an elongated structure that includes, a proximal portion 16, distal portion 18, and an ultrasound transducer 20. In some embodiments, the proximal portion 16 can include a distal connective portion 17 and a proximal connective portion 15. For example, a proximal end of the proximal connective portion 15 can be connected to the handle assembly 14; a distal end of the proximal connective portion 15 can be connected to a proximal end of the distal connective portion 17 and a distal end of the distal connective portion 17 can be connected to a proximal end of the distal portion 18. The ultrasound transducer 20 can be connected to the distal end of the distal portion 18. In some embodiments, the ultrasound transducer 20 can have a particular field of view 22, which can be generated from one side of the ultrasound transducer 20.

In an exemplary application, medical device 10 can be an intracardiac echocardiography (ICE) catheter and can be used to acquire images of the walls of the heart, which may then be registered with a pre-acquired model of the heart. To capture the images, ultrasound transducer 20 transmits ultrasound waves and receives reflections of the transmitted waves from within field of view 22. The reflections can be used to construct an image of anatomical structures, medical devices, and other objects within field of view 22.

In some embodiments, instead of, or in addition to the ultrasound transducer 20, other diagnostic, therapeutic, or mapping devices can be placed at a distal end of the distal portion 18, or along the catheter shaft. For example, a therapeutic device, such as an ablation tip, can be placed at the distal end of the distal portion 18, or mapping devices such as an electromagnetic position sensor (e.g., coil) or electric position sensor (e.g., electrode) can be placed at the distal end of the distal portion 18, or along the catheter shaft 12. Accordingly, one of ordinary skill in the art will recognize and appreciate that the inventive medical device 10 and method of manufacturing the same can be used in any number of diagnostic, therapeutic, and/or mapping applications.

Generally, the length of the distal portion 18 can range from about 2 inches (18.8 mm) to about 6 inches (119.4 mm) and the diameter of the distal portion 18 can range from about 5 French to about 12 French. The diameter of the distal portion 18 can be approximately 7 French in accordance with some embodiments. Although these particular dimensions are mentioned, the dimensions of the distal portion 18 can vary in accordance with various applications of the distal portion 18. The distal portion 18 can be configured for deflection independent of the proximal portion 16. As discussed herein, in some embodiments, the proximal portion 16 can include a proximal connective portion 15 and a distal connective portion 17. In some embodiments, the proximal connective portion 15 and the distal connective portion 17 can have different flexibilities associated with each portion. For example, the proximal connective portion 15 can have a flexibility that is greater (e.g., is more flexible) than the distal connective portion 17. Alternatively, the proximal connective portion 15 can have a flexibility that is less (e.g., is less flexible) than the distal connective portion 17. In some embodiments, the distal connective portion 17 and the proximal connective portion 15 can have a same flexibility.

The ultrasound transducer 20 can be affixed to a distal end of the distal portion 18 in a number of ways. For instance, the ultrasound transducer 20 may be bonded to an inner and/or outer radial surface of the distal portion using an epoxy material. As used herein, the term "radial surface" means a surface at a radial distance from a central axis or a surface developing uniformly around a central axis (for example, but without limitation, an arcuate surface, an annular surface, and/or a cylindrical surface).

The distal portion 18 can include one or more lumens that are disposed along a length of the distal portion 18. In some embodiments, the one or more lumens can be provided for passage of components associated with the transducer 20 (e.g., wires) or other devices positioned at the distal end of the distal portion 18.

The proximal portion 16 can also include one or more lumens. The proximal portion 16 can be constructed of a series of polymer layer(s) and braid structure(s). In particular, one or more wires wound to form a cylindrical braid structure can substantially surround the one or more lumens of proximal portion 16. In addition, a polymeric material, such as polyurethane, nylon, or various types of plastic materials such as polyether block amides offered under the trademark PEBAX®, or any other suitable material, can also substantially surround the one or more lumens of proximal portion 16. The material can have the capability to be displaced and/or to shrink when subjected to a process, such as for example, a heating process that is performed. The mechanical properties of the proximal portion 16 can also be varied by varying the properties of the cylindrical braid structure(s) and the polymeric material (e.g., dimension of the cylindrical braid structure and/or durometers of the polymers). Additionally, the mechanical properties of the proximal portion 16, can be varied along the length of the proximal portion 16 in accordance with some embodiments of the disclosure. Alternatively, the mechanical properties of the proximal portion 16 can be substantially constant along the entire length of the proximal portion 16, in accordance with some embodiments of the disclosure.

The handle assembly 14 can be coupled to the proximal portion 16 at its proximal end (disposed within handle assembly 14 and not shown). The handle assembly 14 can be operative to, among other things, effect movement (i.e., deflection) of the catheter shaft 12. The handle assembly 14 includes a distal end 24 and a proximal end 26. The handle assembly 14 includes one or more actuators (e.g., actuators 29, 30) that can be selectively manipulated to cause catheter shaft 12 to deflect in one or more directions (e.g., up, down, left, and right). In some embodiments, the distal portion 18 can be configured for bi-directional deflection in a first deflection plane, in a direction of arrow 28 (e.g., left, right), and the proximal portion 16 of the catheter shaft 12 can be configured for bi-directional deflection in a second deflection plane, in a direction of arrow 27 (e.g., up, down). For example, the proximal portion 16 can deflect (e.g., up, down), in an opposite direction of the distal portion 18 (e.g., left, right). In some embodiments, one of the actuators 29, 30 can control deflection of the proximal portion 16 and the other one of the actuators 29, 30 can control deflection of the distal portion 18.

In some embodiments of the present disclosure, the distal portion 18 can achieve a small radius of curvature in the first deflection plane in relation to the proximal portion 16, such that the transducer can be deflected from side to side. The proximal portion 16 can achieve a larger radius of curvature with respect to the distal portion 18 in the second deflection plane. In some embodiments, an amount of force necessary to achieve the small radius of curvature in the distal portion 18 can be decreased, as a result of how the proximal portion 16 and the distal portion 18 are constructed.

In addition, as a result of how the proximal portion 16 and the distal portion 18 are constructed, an amount of force requisite for the distal portion 18 to attain the small radius of curvature can be decoupled from the proximal portion 16. For example, an amount of force can be applied to the distal portion 18 (e.g., via pullwires) to attain the small radius of curvature in the first plane, while providing minimal or no deflection of the proximal portion 16 in the second plane. In addition, an amount of force can be applied to the proximal portion 16 (e.g., via pullwires) to attain the larger radius of curvature in the second plane, while providing minimal or no deflection of the distal portion 18 in the first plane. In some embodiments, the ultrasound transducer 20 can be aimed through deflection of the distal portion 18 and the proximal portion 16, while allowing for discreet radius of curvatures for the distal portion 18 and the proximal portion 16 along the first plane and second plane, respectively.

Figure 2A:
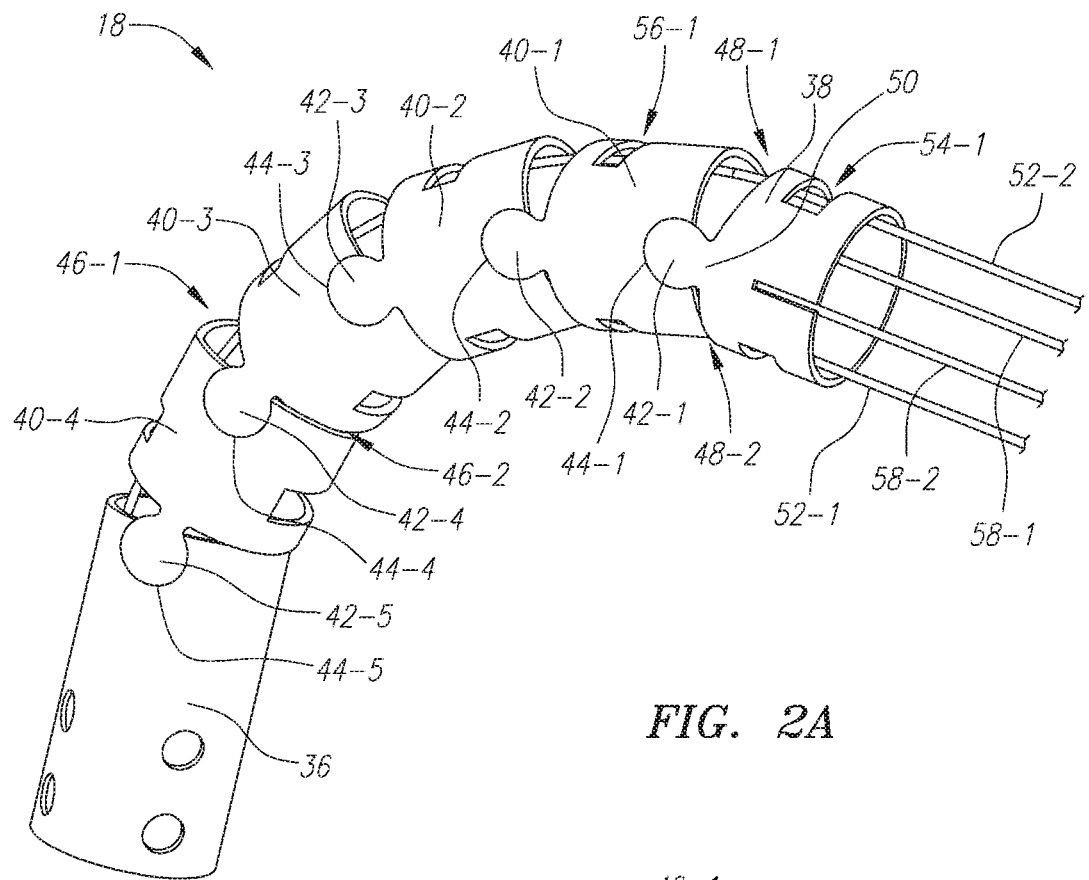
FIG. 2A is an isometric side and top view of a distal portion of a catheter shaft, in accordance with embodiments of the present disclosure.

FIG. 2A is an isometric side view of a distal portion 18 of a catheter shaft 12, in accordance with embodiments of the present disclosure. As discussed herein, the catheter shaft 12 can include an elongated structure that includes a distal portion 18, and a proximal portion 16. In some embodiments, the distal portion 18 can include a distal tip 36, a proximal connector 38, and a plurality of pivoting hollow cylindrical segments 40-1, 40-2, 40-3, 40-4 disposed between the proximal connector 38 and the distal tip 36 along a longitudinal axis that extends through the elongated structure of the catheter shaft 12. The pivoting hollow cylindrical segments 40-1, 40-2, 40-3, 40-4 are hereinafter generally referred to herein as the plurality of pivoting hollow cylindrical segments 40.

In some embodiments, the pivoting hollow cylindrical segments 40 can be formed from a semi-rigid and/or rigid material, such that the pivoting hollow cylindrical segments 40 can generally maintain their shape. In an example, the plurality of pivoting hollow cylindrical segments 40 can be formed from a rigid material, such as a metal (e.g., nitinol, stainless steel). In some embodiments, the distal tip 36 and the proximal connector 38 can also be hollow cylindrical segments formed from a semi-rigid and/or rigid material. For example, the distal tip 36 can be a distal hollow cylindrical segment and the proximal connector 38 can be a proximal hollow cylindrical segment. Thus, an elongate lumen can extend through the proximal connector 38, through the plurality of pivoting hollow cylindrical segments 40, and through the distal tip 36.

The proximal connector 38 can have a proximal and distal face and can be configured to connect with the proximal portion 16 of the catheter shaft 12. The proximal face of the proximal connector 38 can be connected to the proximal portion 16 of the catheter shaft 12, and/or an outer radial surface and/or inner radial surface of the proximal connector 38 can be configured to connect with the proximal portion 16. For example, the proximal portion 16 can be attached via an epoxy to the proximal face, the outer radial surface, and/or inner radial surface of the proximal connector 38.

In some embodiments, a plurality of connections can be disposed along diametrically opposed sides of the distal portion 18 and can be configured to connect the distal tip 36, the plurality of pivoting hollow cylindrical segments 40, and the proximal connector 38. As depicted in FIG. 2A, each of the plurality of connections can include a male connection 42-1, 42-2, 42-3, 42-4, 42-5, hereinafter generally referred to as male connections 42. Further, as depicted in FIG. 2A, each of the plurality of connections can include a female connection 44-1, 44-2, 44-3, 44-4, 44-5, hereinafter generally referred to as female connections 44. Each of the plurality of pivoting hollow cylindrical segments 40, the distal tip 36, and the proximal connector 38 can have a proximal face and a distal face. The male connection 42 can be a longitudinally extending projection disposed on at least one of the adjoining faces between the proximal connector 38 and the most proximal pivoting hollow cylindrical segment 40-1 and at least one of the adjoining faces between the distal tip 36 and the most distal pivoting hollow cylindrical segment 40-4. Additionally, the male connection 42 can be disposed on at least one of the adjoining faces between each of the pivoting hollow cylindrical segments 40.

Faces (e.g., adjoining faces) of the distal tip 36, the pivoting hollow cylindrical segments 40, and the proximal connector 38 that correspond to faces with the male connection 42 can have a female connection 44. In an example, the female connection 44 can be a socket, in some embodiments, that corresponds to and/or accepts the male connection 42, as depicted in FIG. 2A. Thus, adjacent faces can have a first and second socket that corresponds to the first and second male connection 42 (e.g., first and second longitudinally extending projections). In some embodiments, the male connection 42 can include a rounded longitudinally extending projection and the female connection 44 can include an inwardly shaped recess that is configured to surround the rounded longitudinally extending projection more than 180 degrees. By surrounding the rounded projection more than 180 degrees, the male connection 42 and the female connection 44 can be locked together, such that they cannot be pulled apart along the longitudinal axis.

In some embodiments, the male connection 42 and the female connection 44 can form a hinge that can connect the proximal connector 38, the plurality of pivoting hollow cylindrical segments 40, and/or the distal tip 36. The hinge can allow the distal portion 18 to deflect bi-directionally, as further discussed herein. In an example, a plurality of diametrically opposed hinges can be formed on a first side and a second side of the distal portion 18 and can be configured to connect the proximal connector 38, the plurality of pivoting hollow cylindrical segments 40, and the distal tip 36.

Figure 2B:
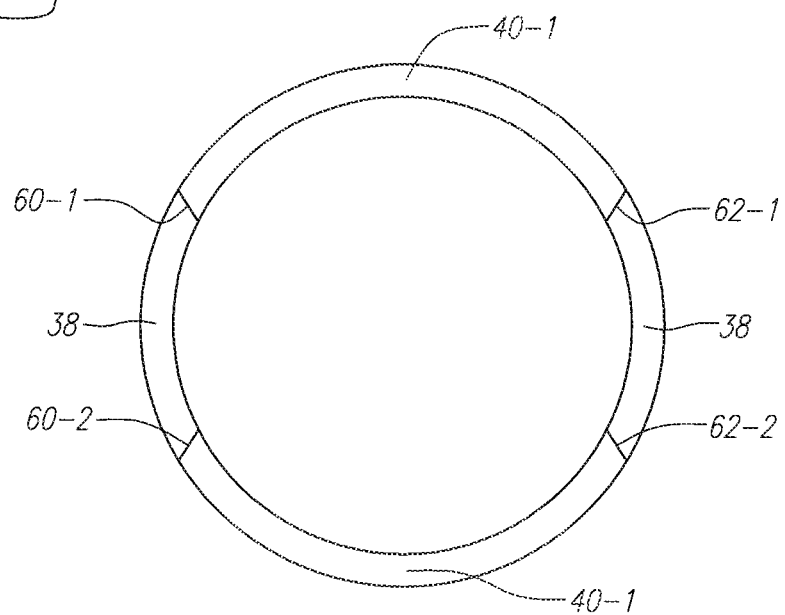
FIG. 2B is a cross-sectional view of the distal portion of the catheter shaft, in accordance with embodiments of the present disclosure.

In addition, the male connection 42 and the female connection 44 can be cut to center, such that the male connection 42 and the female connection 44 cannot move laterally, along an elongate axis extending through the distal portion 18, with respect to one another and separate. FIG. 2B is a cross-sectional view of the distal portion 18 of the catheter shaft 12, in accordance with embodiments of the present disclosure. In particular, FIG. 2B depicts a cross-sectional view of pivoting hollow cylindrical segment 40-1. In some embodiments, a laser can form cuts 60-1, 60-2, 62-1, 62-2 in a sidewall of a hollow cylindrical tube to form the male connection 42-1 that extends from proximal connector 38 and the female connection 44-1 that is formed in the pivoting hollow cylindrical segment 40-1. In an example, the cuts 60-1, 60-2, 62-1, 62-2 can be angled toward a central axis of the hollow cylindrical tube, as shown. In an example, the cuts 60-1, 60-2, 62-1, 62-2 can be made on diametrically opposed sides of the hollow cylindrical tube. The cuts 60-1, 60-2 can be part of a same cut made on one side of the hollow cylindrical tube and the cuts 62-1, 62-2 can be part of a same cut made on another side of the hollow cylindrical tube. For example, the cuts 60-1, 60-2 and 62-1, 62-2 can extend around an outer perimeter of the male connection 42-1 and an inner perimeter of the female connection 44-1.

The cuts 60-1, 60-2 on a first side can be angled towards the central axis of the hollow cylindrical tube and the cuts 62-1, 62-2 on a second side can also be angled towards the central axis of the hollow cylindrical tube. As such, the cuts 60-1, 60-2 on a first side can be made at an angle that is opposite to the cuts 62-1, 62-2 on an opposite side of the hollow cylindrical tube.

In some embodiments, each adjoining face between the distal tip 36, the plurality of pivoting hollow cylindrical segments 40, and the proximal connector 38 can include at least one male connection 42 and one female connection 44. For example, a proximal face of the distal tip 36 can include two female connections, two male connections, or a female connection and a male connection. Accordingly, the distal face of the most distal pivoting hollow cylindrical segment 40-4 can have connections that correspond to the proximal face of the distal tip 36. Likewise, the distal face of the proximal connector 38 can include two female connections, two male connections, or a female connection and a male connection. Accordingly, the proximal face of the most proximal pivoting hollow cylindrical segment 40-1 can have connections that correspond to the proximal face of the distal tip 36. In addition, each one of the proximal and distal faces of the plurality of pivoting hollow cylindrical segments 40 can include two female connections, two male connections, or a female connection and a male connection. Accordingly, an adjoining face of an adjacent pivoting hollow cylindrical segment can have connections that correspond.

The most proximal pivoting hollow cylindrical segment 40-1 can be disposed next to and can be connected with the proximal connector 38. In an example, the proximal face of the most proximal pivoting hollow cylindrical segment 40-1 can be connected to the distal face of the proximal connector 38 and the distal face of the most proximal pivoting hollow cylindrical segment 40-1 can be connected to the proximal face of the second most proximal pivoting hollow cylindrical segment 40-2. As such, each of the plurality of pivoting hollow cylindrical segments 40 can be connected to one another via proximal and distal faces of each of the plurality of pivoting hollow cylindrical segments 40. In addition, the distal tip 36 can be connected to a most distal one of the pivoting hollow cylindrical segments 40-4 via a proximal face of the distal tip 36 and a distal face of the most distal pivoting hollow cylindrical segment 40-4. For example, the distal tip 36 can be connected to one of the pivoting hollow cylindrical segments 40 via adjacent faces of the distal tip 36 and the most distal one of the pivoting hollow cylindrical segment 40-4; the pivoting hollow cylindrical segments 40 can be connected to one another via their adjacent faces; and the proximal connector 38 can be connected to a most proximal one of the pivoting hollow cylindrical segments 40-1 via their adjacent faces.

In some embodiments, diametrically opposed pivot spaces 46-1, 46-2 and 48-1, 48-2 can be formed 90 degrees opposed to each pair of connections. For example, the pivot spaces can be formed by removing a portion of the proximal and/distal face of each pivoting hollow cylindrical segment 40, proximal face of the distal tip 36, or distal face of the proximal connector 38 between a point on each face that is 90 degrees opposed to the connection (e.g., male connector and female connector) and a base of each connection. For example, as depicted in FIG. 2A, material has been removed on a distal face of the proximal connector 38 between the base 50 of the male connector 42-1 and a point that is 90 degrees opposed to the male connector 42-1 to create the pivot space 48-1.

In an example, the pivot spaces can allow the distal portion 18 to deflect bi-directionally. For instance, the distal portion 18 has been deflected to the left in FIG. 2A, revealing the pivot spaces 46-1, 48-1, for example, and causing the pivot spaces 46-2, 48-2 to close. The distal portion 18, however, can also be deflected to the right, to cause the pivot spaces 46-2, 48-2 to be revealed. In some embodiments, the pivot spaces 46-1, 46-2, 48-1, 48-2 can allow the distal portion to deflect perpendicular to a plane that extends through the plurality of connections. Although pivot spaces 46-1, 46-2, 48-1, 48-2 are discussed, adjacent faces between the distal tip 36, the plurality of pivoting hollow cylindrical segments 40, and the proximal connector 38 can include pivot spaces, as depicted in at least FIG. 2A.

In some embodiments, distal pullwires 52-1, 52-2 can extend from the proximal portion 16 through the distal portion 18. In an example, the distal pullwires 52-1, 52-2 can extend from the handle 14 and can be connected to one of the actuators 29, 30. In some embodiments, the distal tip 36, each of the plurality of pivoting hollow cylindrical segments 40, and the proximal connector 38 can include tabs through which pullwires can extend. For example, the proximal connector 38 and the most proximal pivoting hollow cylindrical segment 40-1 are illustrated as having tabs 54-1, 56-1. The distal pullwires 52-1, 52-2 can extend through a pullwire tunnel created by the tabs in the distal portion 18 and can be connected to the distal tip 36, in some embodiments. The tabs are discussed further herein. In some embodiments, the catheter shaft 12 can include proximal pullwires 58-1, 58-2 that extend through the proximal portion 16 and can be connected to the proximal connector 38 and to an actuator 29, 30 in the handle 14.

In some embodiments, the distal portion 18 can be formed from a unitary piece of material. For example, the distal portion 18 can be formed from a single hollow cylindrical tube, in some embodiments. In an example, diametrically opposed pivot spaces can be formed along two sides of the unitary piece of material. The diametrically opposed pivot spaces can be cut outs that are formed in a sidewall of the hollow cylindrical tube. The diametrically opposed pivot spaces can define a diametrically opposed spine portion that runs along either side of the hollow cylindrical tube. In an example, the diametrically opposed pivot spaces can be formed between the distal tip, an adjacent pivoting hollow cylindrical segment, each of the plurality of pivoting hollow cylindrical segments, and between the proximal connector and an adjacent pivoting hollow cylindrical segment. The diametrically, opposed spine portion can connect the proximal connector, the plurality of pivoting hollow cylindrical segments, and the distal tip and can allow the hollow cylindrical tube to be deflected in a bidirectional manner.

In some embodiments, the hollow cylindrical tube can be made from a semi-rigid and/or flexible material. For example, the hollow cylindrical tube can be made from a polymer, which can allow the diametrically opposed spine to flex between the proximal connector and an adjacent pivoting hollow cylindrical segment, between the plurality of hollow cylindrical segments, and between the distal tip and an adjacent pivoting hollow cylindrical segment.

In some embodiments, the proximal connector, the plurality of pivoting hollow cylindrical segments, and/or the distal tip can have tabs that are formed in a manner such as that discussed herein, which can create pullwire tunnels through the distal portion. The tabs are discussed further in relation to FIGS. 3A to 3E. In an example, pullwires can pass through the pullwire tunnels and can be attached to the distal tip. The pullwire tunnels that are formed via the tabs can allow for movement of a pullwire through each tunnel, allowing the distal portion to deflect.

Figure 3A:
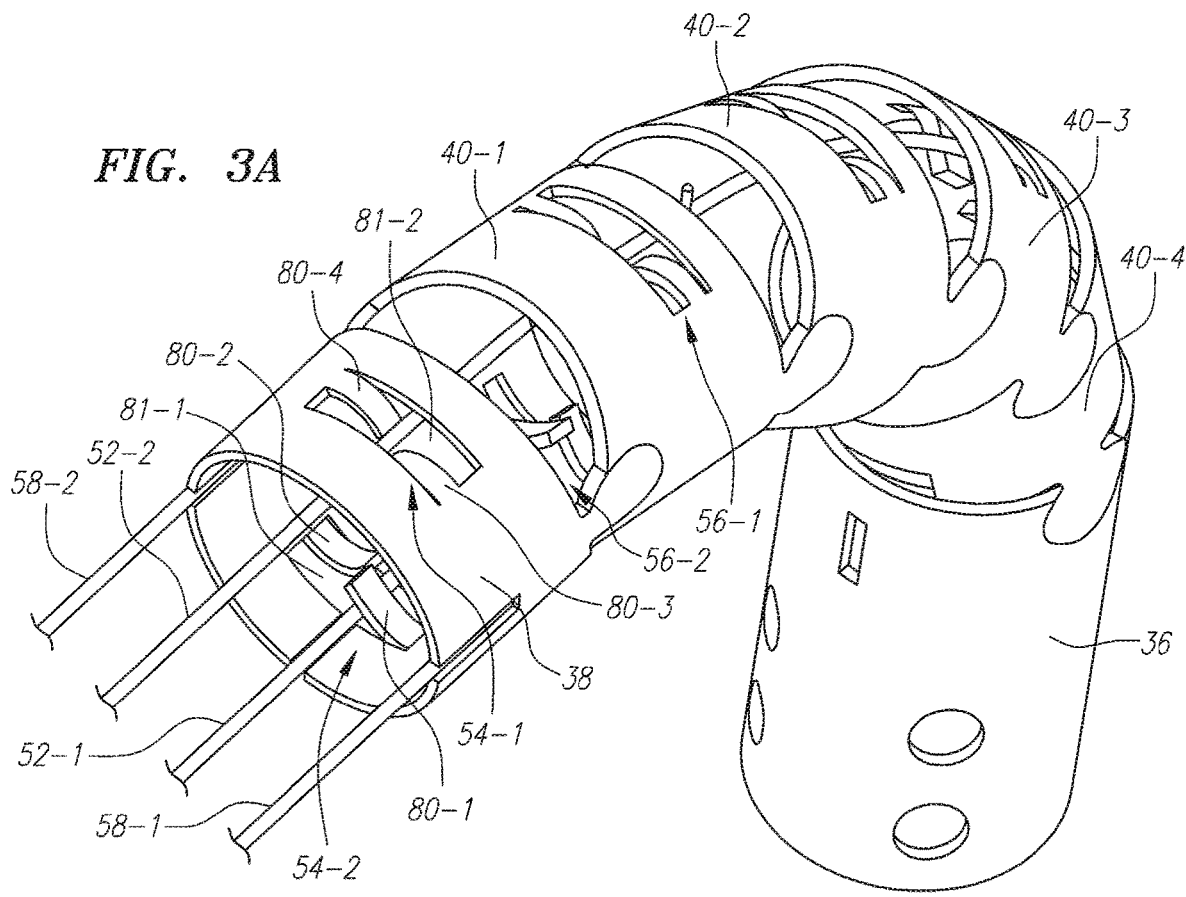
FIG. 3A is an isometric side and bottom view of a distal portion of a catheter shaft looking distally, in accordance with embodiments of the present disclosure.

FIG. 3A is an isometric side and bottom view of a distal portion of a catheter shaft 12 looking distally and depicts pairs of diametrically opposed tabs 54-1, 54-2 and 56-1, 56-2, in accordance with embodiments of the present disclosure. As depicted, the diametrically opposed pair of tabs 54-1, 54-2 is shown on the proximal connector 38 and the diametrically opposed pair of tabs 56-1, 56-2 is shown in the most proximal pivoting hollow cylindrical segment 40-1. In some embodiments, a diametrically opposed pair of tabs 56-1, 56-2 can extend from an inner wall of each of the plurality of pivoting hollow cylindrical segments 40. In some embodiments, diametrically opposed pairs of tabs can extend from the distal tip 36. The diametrically opposed pairs of tabs can be 90 degrees opposed to the connections (e.g., hinges), in some embodiments. For example, as depicted, the diametrically opposed pair of tabs 54-1, 54-2 can be 90 degrees opposed to the connections (e.g., male female connections) between the proximal connector 38 and the most proximal pivoting hollow cylindrical segment 40-1. However, the diametrically opposed pair of tabs 54-1, 54-2 can be more or less opposed to the connections than 90 degrees. In an example, the tabs can run along the same side of the distal portion 18, as depicted in FIG. 3A.

Figure 3B:
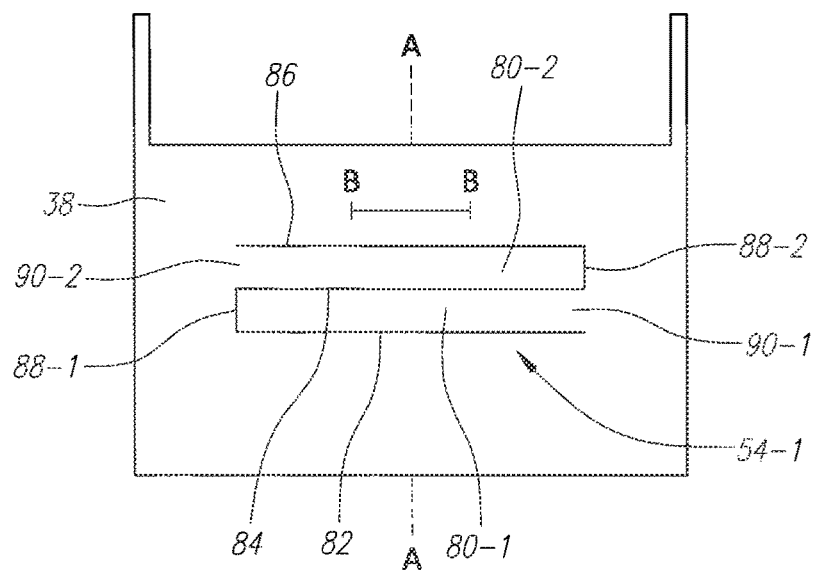
FIG. 3B is a side view of a proximal connector and depicts a tab, in accordance with embodiments of the present disclosure.

FIG. 3B is a side view of a proximal connector 38 and depicts a tab 54-1, in accordance with embodiments of the present disclosure. Although proximal connector 38 is discussed in relation to FIG. 3B, the pivoting hollow cylindrical segments 40 and/or the distal tip 36 can include the same or similar features as those discussed in relation to the proximal connector 38. The tab 54-1 can include a proximal finger 80-1 and a distal finger 80-2 that are adjacently opposed to one another. For example, the proximal finger 80-1 and the distal finger 80-2 may not be directly opposed to one another, in some embodiments. As illustrated in FIG. 3A, the proximal finger 80-1 and the distal finger 80-2 can be adjacently opposed to one another, such that portions of the proximal finger 80-1 and the distal finger 80-2 are adjacent to one another and/or touch, in some embodiments.

In some embodiments, the proximal finger 80-1 and the distal finger 80-2 can be formed by making cross-longitudinal cuts in a wall of each of the proximal connector 38, the plurality of pivoting hollow cylindrical segments 40, and/or the distal tip 36. As such, the tabs (e.g., tab 54-1) and the proximal finger 80-1 and the distal finger 80-2 can be defined by cross-longitudinal cuts made in a wall of the proximal connector 38. For example, when the proximal connector 38 is a hollow cylindrical segment, a cut can be made from an outer radial surface of the proximal connector 38 partially or all the way through the proximal connector 38 to the inner radial surface of the proximal connector 38. In some embodiments, a proximal cross-longitudinal cut 82 can be made in the proximal connector 38, a middle cross-longitudinal cut 84 can be made in the proximal connector 38 and a distal cross-longitudinal cut 86 can be made in the proximal connector 38.

The cross-longitudinal cuts can be made perpendicular to the longitudinal axis defined by dotted line AA and can define each tab (e.g., tab 54-1). In some embodiments, the cross-longitudinal cuts can be between parallel and perpendicular to the longitudinal axis AA of the proximal connector 38. For example, each of the cross-longitudinal cuts can be disposed at an angle to the longitudinal axis that is greater than or less than 90 degrees. The longitudinal axis AA can extend through the distal portion 18 and cross-longitudinal cuts can be made in each of the pivoting hollow cylindrical segments 40 and/or distal tip 36, in addition to the proximal connector 38. Thus, cross-longitudinal cuts can be made in the proximal connector 38 and can be perpendicular to a longitudinal axis AA of the proximal connector 38, each of the plurality of pivoting hollow cylindrical segments 40, and/or the distal tip 36.

Figure 3C:
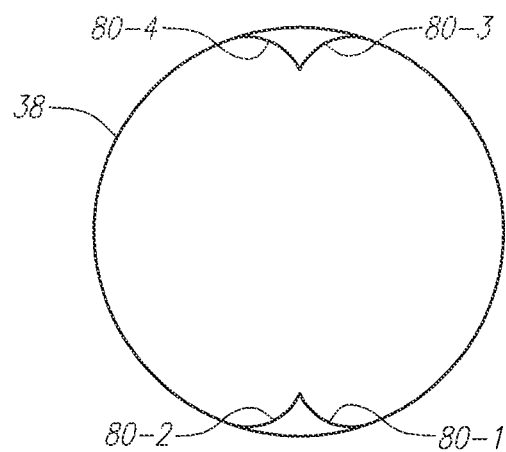
FIG. 3C is a front cross-sectional view that depicts a first tab configuration, in accordance with embodiments of the present disclosure.

In some embodiments, the proximal finger 80-1 and the distal finger 80-2 can be bent inwardly and away from an inner radial surface of the proximal connector 38. For example, a tip 88-1, 88-2 of each finger 80-1, 80-2 can be curved inwardly toward the longitudinal axis defined by line AA, as depicted in FIG. 3A and FIG. 3C. For instance, each finger 80-1, 80-2 can extend outwardly from a base 90-1, 90-2 of each finger 80-1, 80-2 and can be gradually curved toward the longitudinal axis AA. In some embodiments, the inwardly bent finger 80-1, 80-2 (and fingers 80-3, 80-4 depicted in FIG. 3A) can be curved toward the longitudinal axis AA, as depicted in FIG. 3A and FIG. 3C. In an example, each inwardly bent finger 80-1, . . . , 80-4 can form a concave shape with respect to an inner radial surface of the proximal connector 38. The tips 88-1, 88-2 of the proximal finger 80-1 and the distal finger 80-2 can be adjacent to one another and/or can be connected to one another, in some embodiments. For example, as depicted in FIG. 3A, tips of the proximal finger and the distal finger can be connected via an adhesive, such as an epoxy, and/or the proximal finger and the distal finger can be connected via a welding process. As depicted in FIG. 3B, the proximal finger and the distal finger 80-1, 80-2 can be inwardly bent and can be connected to one another along line BB.

Figure 3D:
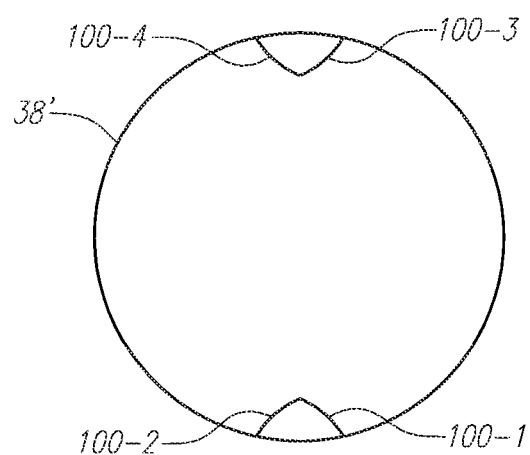
FIG. 3D is a front cross-sectional view that depicts a second tab configuration, in accordance with embodiments of the present disclosure.

FIG. 3D is a front cross-sectional view that depicts a second tab configuration, in accordance with embodiments of the present disclosure. In some embodiments, each finger 100-1, 100-2, 100-3, 100-4 can have an inverse curve. For example, each finger 100-1, 100-2, 100-3, 100-4 can have an inverse curve of that depicted in FIG. 3A and FIG. 3C. For instance, each finger 100-1, 100-2, 100-3, 100-4 can be curved down and away from a base of each finger and toward a tip of the adjacently opposed finger, such that tips of each finger 100-1, 100-2, 100-3, 100-4 are located adjacent to one another. In some embodiments, as depicted in FIG. 3D, each finger 100-1, 100-2, 100-3, 100-4 can form a concave shape with respect to an inner radial surface of the proximal connector 38'. In an example, the tips of each finger 100-1, 100-2, 100-3, 100-4 can be connected to one another. For instance, the tips of each finger 100-1, 100-2, 100-3, 100-4 can be connected with an epoxy and/or can be welded together, in some examples.

Figure 3E:
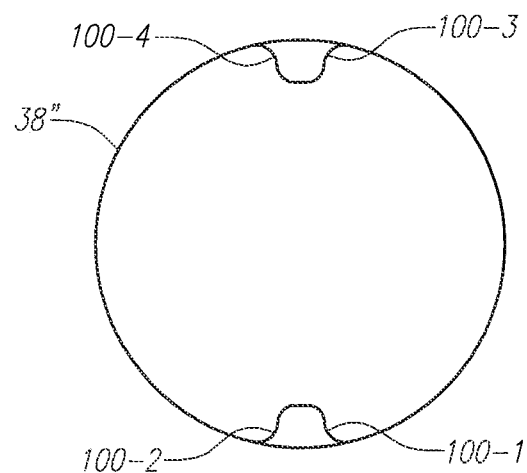
FIG. 3E is a front cross-sectional view that depicts a third tab configuration, in accordance with embodiments of the present disclosure.

FIG. 3E is a front cross-sectional view that depicts a third tab configuration, in accordance with embodiments of the present disclosure. In some embodiments, each finger 102-1, 102-2, 102-3, 102-4 can be bent in a compound shape with respect to an inner radial surface of the proximal connector 38". For example, progressing from a base of each finger 102-1, 102-2, 102-3, 102-4 to a tip of each finger 102-1, 102-2, 102-3, 102-4, the finger 102-1, 102-2, 102-3, 102-4 can be bent in a concave shape near the base, which can transition into a concave shape near the tip of each finger 102-1, 102-2, 102-3, 102-4. As discussed herein, the tips of each finger 102-1, 102-2, 102-3, 102-4 can be connected to each other and, as depicted in FIG. 3E, the connected fingers 102-1, 102-2, 102-3, 102-4 can form a bell shape.

In some embodiments, the plurality of pivoting hollow cylindrical segments 40 and the distal tip 36 can have tab configurations that are the same or similar to the tab configuration discussed in relation to FIGS. 3A to 3E. For example, the plurality of pivoting hollow cylindrical segments 40 and the distal tip 36 can have tab configurations that are the same or similar to those included on the proximal connector 38. In some embodiments, the cross-longitudinal cuts 82, 84, 86, depicted in FIG. 3B can be formed in each of the proximal connector 38, the plurality of pivoting hollow cylindrical segments 40, and/or the distal tip 36. A punch and/or press can be used to bend the fingers 80-1, 80-2 toward the longitudinal axis AA. In an example, the punch can include a punch head that contacts each of the fingers 80-1, 80-2. The punch head can include a complimentary surface to each of the tab configurations depicted in FIGS. 3C to 3E. For instance, the punch head can include a concave, convex, and/or compound curve to form the various tab configurations depicted in FIGS. 3C to 3E. After the cross-longitudinal cuts 82, 84, 86 have been made, the punch can be used to depress the fingers 80-1, 80-2 towards the longitudinal axis AA and form a pullwire tunnel.

In some embodiments, a first and second pullwire tunnel 81-1, 81-2 can be formed by the diametrically opposed pair of tabs 54-1, 54-2 that extend from the inner wall of each of the hollow cylindrical segments (e.g., proximal connector 38). A first distal pullwire 52-1 and a second distal pullwire 52-2 can extend through the first pullwire tunnel 81-1 and the second pullwire tunnel 81-2.

In some embodiments, a length of the cross-longitudinal cuts 82, 84, 86 can be selected based on a desired size of the first and/or second pullwire tunnels 81-1, 81-2. For example, as a length of the cross-longitudinal cut is increased, a diameter of the pullwire tunnels 81-1, 81-2 can be increased. For instance, a length of the proximal finger 80-1 and the distal finger 80-2 can be increased as a result of the longer cross-longitudinal cut, allowing for a larger pullwire tunnel to be formed by the proximal finger 80-1 and the distal finger 80-2. For example, in some embodiments, the fingers 80-1, 80-2 can be deformed to create pullwire tunnels 81-1, 81-2, as discussed herein.

In some embodiments, the diametrically opposed pair of tabs 54-1, 54-2 can be configured to accept the first distal pullwire 52-1 and the second distal pullwire 52-2. The first distal pullwire 52-1 and the second distal pullwire 52-2 can be connected to the handle assembly 14. In some embodiments, the handle assembly 14 can include an actuator (e.g., actuator 29) that can be selectively manipulated to apply tension to the first pullwire 82-1 and the second pullwire 82-2 that pass from the proximal portion 16 to the distal portion 18. In an example, a proximal end of the first distal pullwire 52-1 and the second distal pullwire 52-2 can be connected to the actuator 29. The first distal pullwire 52-1 and the second distal pullwire 52-2 can extend from the handle assembly 14, through the proximal portion 16, to the distal portion 18. In an example, the proximal portion 16 can include pullwire lumens that house the distal pullwires 52-1, 52-2.

The first distal pullwire 52-1 and second distal pullwire 52-2 can extend through the distal portion 18 and can be connected to a distal end of the distal portion 18, in some embodiments. For example, the first distal pullwire 52-1 and second distal pullwire 52-2 can be connected to the distal tip 36, which can serve as a distal pull ring. As such, in some embodiments, the distal tip 36 can serve as a pull ring. Accordingly, when the first distal pullwire 52-1 and the second distal pullwire 52-2 are selectively tensioned (e.g., via actuator 29), the distal tip 36 can deflect hi-directionally in a direction of arrow 28. In an example, the distal tip 26, along with the distal portion 18 can be configured to deflect along a plane that extends through the first distal pullwire 52-1 and the second distal pullwire 52-2 (e.g., parallel and/or coplanar with the plane) and can deflect perpendicular to a plane that extends through the plurality of connections when tension is applied to at least one of the first distal pullwire 52-1 and the second distal pullwire 52-2. For instance, when tension is applied to at least one of the first distal pullwire 52-1 and the second distal pullwire 52-2, the connections connecting each of the plurality of pivoting hollow cylindrical segments can allow each of the plurality of pivoting hollow cylindrical segments to deflect hi-directionally.

In some embodiments, the proximal portion 16 can include a proximal set of pullwires 58-1, 58-2. In an example, the proximal set of pullwires 58-1, 58-2 can include a first proximal pullwire 58-1 and a second proximal pullwire 58-2. In an example, a proximal end of the first and second proximal pullwires 58-1, 58-2 can be connected to the handle assembly 14. For instance, the proximal end of the first and second proximal pullwires 58-1, 58-2 can be connected to actuator 30. The proximal set of pullwires 58-1, 58-2 can be diametrically opposed to one another and 90 degrees opposed to the first distal pullwire 52-1 and the second distal pullwire 52-2.

The first and second proximal pullwires 58-1, 58-2 can extend from the handle assembly 14 through the proximal portion 16 and can be connected to a distal end of the proximal portion 16 and/or the proximal connector 38 in the distal portion 18. In an example, the proximal connector 38 can serve as a proximal pull ring. Accordingly, when the first proximal pullwire 58-1 and the second proximal pullwire 58-2 are selectively tensioned (e.g., via actuator 30), the proximal portion 27 can deflect hi-directionally in a direction of arrow 27. In an example, the proximal portion 16 can deflect along a plane that extends through the first proximal pullwire 58-1 and the second proximal pullwire 58-2 when tension is applied to at least one of the first proximal pullwire 58-1 and the second proximal pullwire 58-2. Thus, the proximal portion 16 can be deflected in an opposite direction as the distal portion 18.

In some embodiments, the proximal portion 16 can be decoupled from the distal portion 18. For example, a deflection force can be effected on the distal portion 18 to deflect the distal portion 18, however, the deflection force effected on the distal portion 18 may not cause the proximal portion 16 to deflect and/or may cause the proximal portion 16 to only minimally deflect. The configuration of the distal portion 18 can allow for a decreased force necessary to achieve angulation of the distal portion 18 versus the proximal portion 16.

The proximal portion 16 can include a quad lumen through which the first distal pullwire 52-1 and the second distal pullwire 52-2 can pass through to the distal portion 18 and the first proximal pullwire 58-1 and the second proximal pullwire 58-2 can pass through to the distal end of the proximal portion 16 and/or the proximal connector 38 to which they are connected. One or more layers can be formed around the quad lumen. For example, one or more layers of a polymer can be formed around the quad lumen to adjust mechanical properties of the proximal portion 16. In some embodiments, a number of compression coils can be disposed in the proximal portion 16. The number of compression coils can be formed of stainless steel, in some embodiments, and can be disposed around the first proximal pullwire 58-1 and the second proximal pullwire 58-2. The compression coils can be included in the proximal portion 16 to alter a deflection force necessary to deflect the proximal portion 16. In some embodiments, the deflection force necessary to deflect the proximal portion 16 can be greater than a deflection force necessary to deflect the distal portion 18.

In addition, because the first distal pullwire 52-1 and the second distal pullwire 52-2 pass through the proximal portion 16 and are not connected to the proximal portion 16, the first distal pullwire 52-1 and the second distal pullwire 52-2 can be tensioned to deflect the distal portion 18 without deflecting or minimally deflecting the proximal portion 16. Thus, the distal portion 18 can be deflected independently of the proximal portion 16. Additionally, because the first and second pair of distal pullwires 52-1, 52-2 and the first and second pair of proximal pullwires 58-1, 58-2 are 90 degrees opposed to one another and are attached at points that are 90 degrees opposed to one another (e.g., on the distal tip and the proximal connector), the distal portion 18 can be deflected in a different direction than the proximal portion 16.

Some approaches have employed catheters with four pullwires attached at a single distal point, for example, a pull ring. The pullwires can be 90 degrees opposed to one another around the pull ring. The shaft of the catheter can include materials of varying rigidity to promote generally desired angulation of the shaft. Angulation in one plane occurs when one of two diametrically opposed pullwires is pulled and on another plane when one of the other two diametrically opposed pullwires are pulled. In an example where an ultrasound transducer is connected to a distal end of the catheter, the approach can be effective for aiming the ultrasound transducer, but may not allow for discreet angulation radii on the two planes. However, due to the decoupling effect between the proximal portion 16 and the distal portion 18, in embodiments of the present disclosure, the proximal portion 16 and the distal portion 18 can have discreet angulation radii. For example, an anchoring point at the distal tip 36 can be axially offset from an anchoring point at the proximal connector 36, which when combined with the configuration of the distal portion 18, can allow for decoupling between the proximal portion 16 and the distal portion 18.

Figure 4:
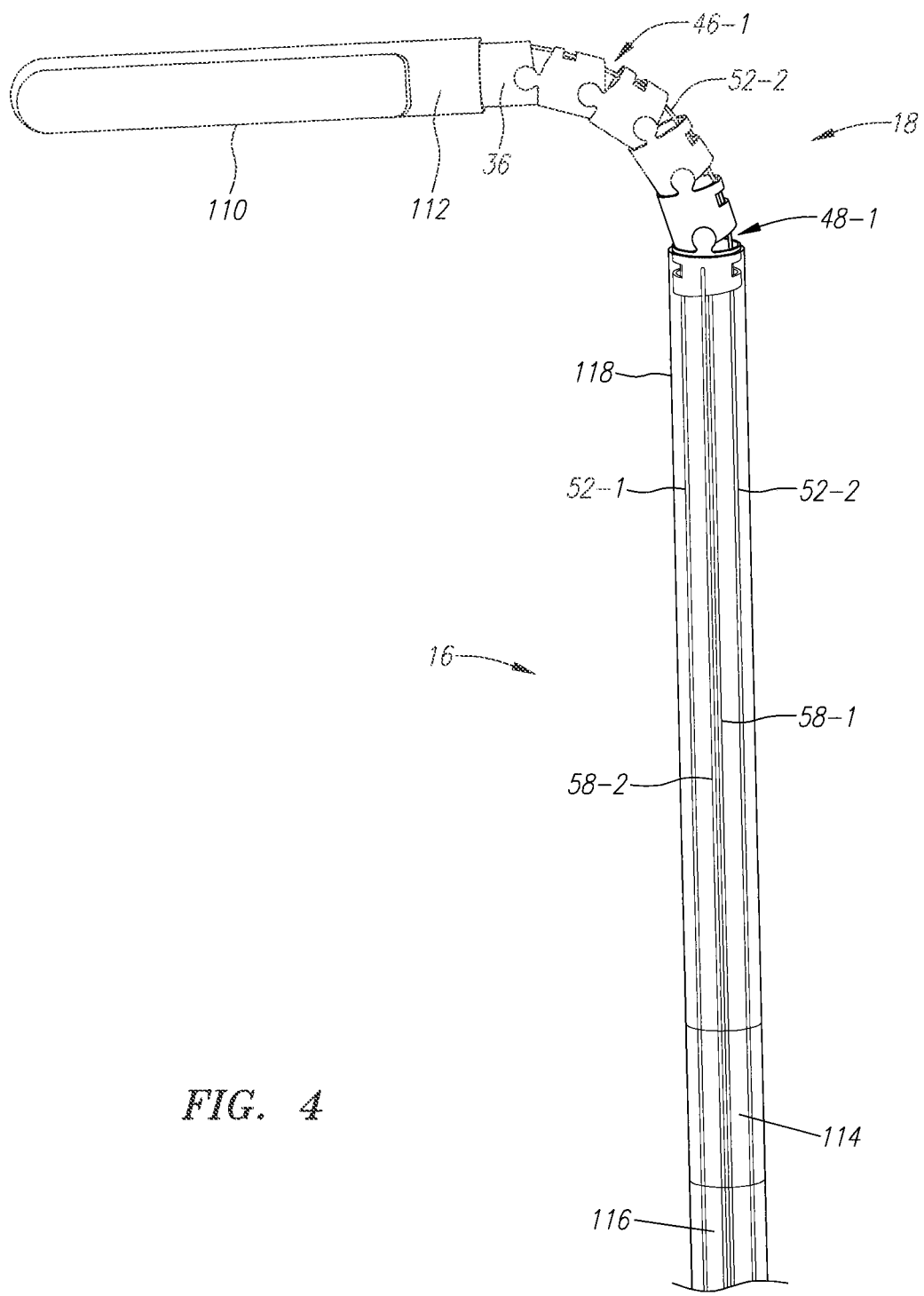
FIG. 4 is a side view of an ultrasound transducer connected to a distal portion of a catheter shaft, which is connected to a proximal portion of the catheter shaft, in accordance with embodiments of the present disclosure.

FIG. 4 is a side view of an ultrasound transducer 110 connected to a distal portion 18 of a catheter shaft 12, which is connected to a proximal portion 16 of the catheter shaft 12, in accordance with embodiments of the present disclosure. In an example, the ultrasound transducer 110 can include a proximal end 112 that can be configured to connect with the distal tip 36 of the distal portion 18 of the catheter shaft 12. In some embodiments, an outer radial surface of the distal tip 36 can be connected with an inner radial surface of the proximal end 112 of the ultrasound transducer 110. In some embodiments, a field of view 22 of the ultrasound transducer 110 can be directed perpendicular to a deflection plane associated with the distal portion 18. Thus, as the distal portion 18 is deflected, the field of view 22 of the ultrasound transducer 110 can be moved across tissue, for example.

As depicted in FIG. 4, the distal end of the proximal portion 16 is connected to the proximal end of the distal portion 18. In some embodiments, as discussed herein, the distal end of the proximal portion 16 can be connected to the proximal connector 38 of the distal portion 18. In an example, an inner radial surface of the proximal portion 16 can be connected with an outer radial surface of the proximal end of the distal portion 18 (e.g., outer radial surface of the proximal connector 38).

Figure 5A:
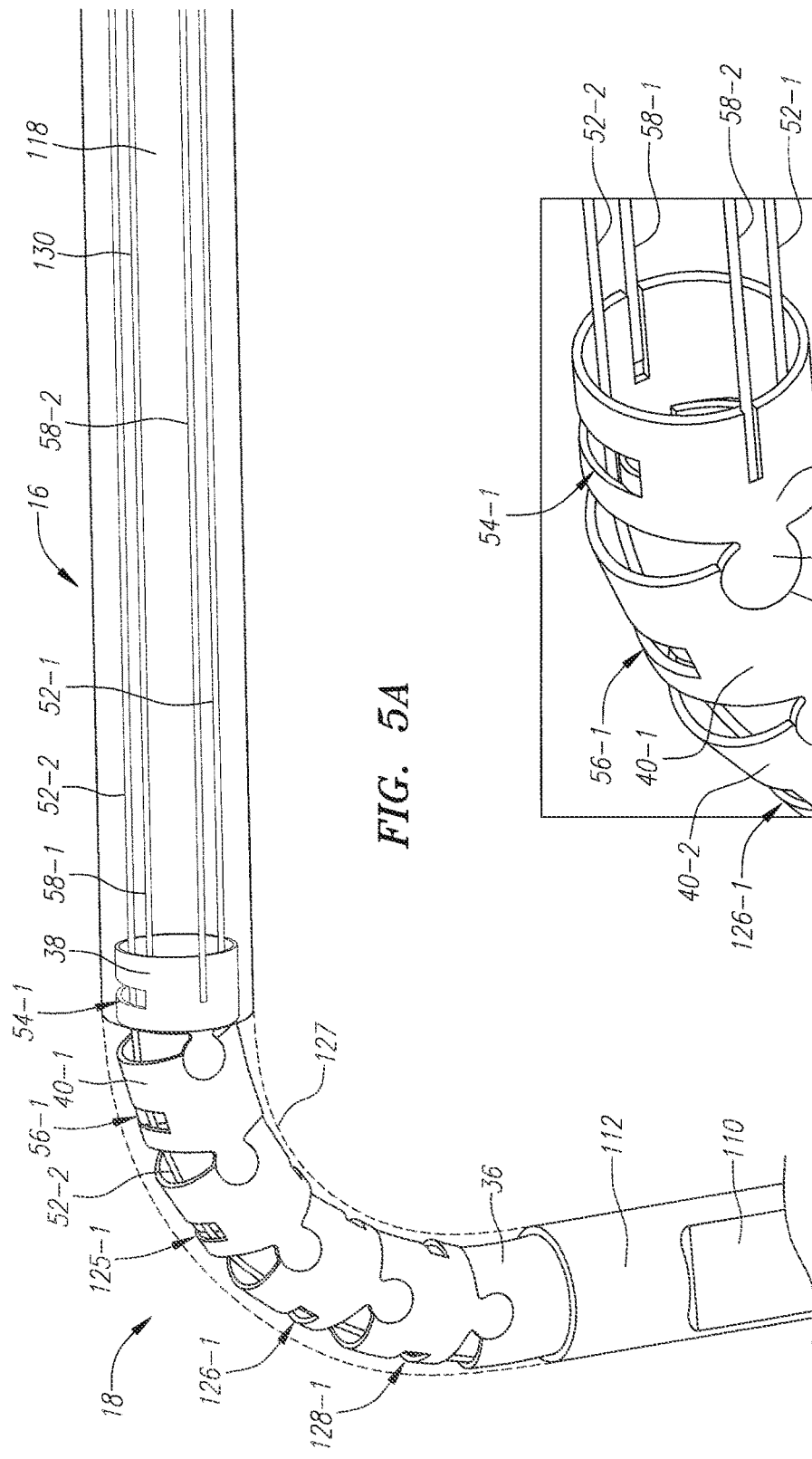
FIG. 5A is a side view of the ultrasound transducer, the distal portion, and the proximal portion of the catheter shaft, in accordance with embodiments of the present disclosure.

In some embodiments, a covering 127 (as depicted in FIG. 5A) can be disposed over the distal portion 18. The covering 127 can be made from a flexible material (e.g., latex) and can extend over an exposed section of the distal portion 18 between the distal end of the proximal portion 16 and the proximal end 112 of the ultrasound transducer 110. The covering 127 can flex as the distal portion 18 flexes and can prevent tissue and/or other foreign matter from becoming lodged in the pivot spaces 46-1, 48-1 between each of the pivoting hollow cylindrical segments 40 and/or between the proximal connector 38 and an adjacent pivoting hollow cylindrical segment 40-1 and/or between the distal tip 36 and an adjacent hollow cylindrical segment 40-4. In some embodiments, a thickness of the covering 127 can be chosen such that a diameter of the proximal portion 16 is the same as the distal portion 18. In some embodiments, the diameter of the proximal end 112 of the ultrasound transducer 110 can also be the same as the distal portion 18 and the proximal portion 16. In some embodiments, the latex covering 127 can extend over the distal portion 18 and over an outer radial surface of a distal end of the proximal portion 16. In some embodiments, the latex covering 127 can extend over a proximal end 112 of the ultrasound transducer 110.

In some embodiments, the first distal pullwire 52-1 and the second distal pullwire 52-2 can extend through the proximal portion 16 to the distal tip 36, to which they are connected. The first proximal pullwire 58-1 and the second proximal pullwire 58-2 can extend through the proximal portion 16 and can be connected to the proximal connector 38. In some embodiments, each of the pullwires can pass through a pullwire lumen in the proximal portion 16. The first proximal pullwire 58-1 and the second proximal pullwire 58-2 can extend through compression coils 114, in some embodiments. As discussed herein, the compression coils 114 can alter a force required to deflect the proximal portion 16. In addition, the proximal portion 16 can be formed from different layers of material, which can alter a force required to deflect the proximal portion 16. For example, a proximal end of the proximal portion 16 can be partially or wholly formed with a first material 116 and the distal end of the proximal portion 16 can be partially or wholly formed with a second material 118. For example, as discussed herein, the proximal portion 16 can include a proximal connective portion 15 and a distal connective portion 17, as discussed in relation to FIG. 1. In some embodiments, the first material 116 can be of a stiffer durometer than the second material 118. As such, a greater radius of curvature can be formed at a distal end of the proximal portion 16 than the proximal end of the proximal portion 16.

FIG. 5A is a side view of the ultrasound transducer 110, the distal portion 18, and the proximal portion 16 of the catheter shaft, in accordance with embodiments of the present disclosure. As discussed herein, the proximal portion 16 can be connected to the distal portion 18 and the distal portion 18 can be connected to the ultrasound transducer 110. Alternatively, in some embodiments, a different device, other than the ultrasound transducer 110 can be connected to a distal tip 36 of the distal portion 18. As depicted, the first and second proximal pullwires 58-1, 58-2 can extend through the proximal portion 16 and can be connected to the proximal connector 38. The first and second distal pullwires 52-1, 52-2 can extend through the proximal portion 16 and into the distal portion 18 through pullwire tunnels formed by tabs 54-1, 56-1, 125-1, 126-1, 128-1 on the proximal connector 38 and the plurality of pivoting hollow cylindrical segments 40. In some embodiments, the distal tip can also include a tab through which the pullwires pass. Each of the tabs 54-1, 56-1, 125-1, 126-1, 128-1 can have a diametrically opposed corresponding tab on the other side of the distal portion 18, through which the second distal pullwire 52-2 can pass.

As depicted, the first proximal pullwire 58-1 can extend through a compression coil 130, which can alter a deflection of the proximal portion 16 and/or a deflection force associated with deflection of the proximal portion 16. In addition, the first material 116 and/or second material 118 can alter the deflection of the proximal portion 16 and/or the deflection force associated with deflection of the proximal portion 16.

Figure 5B:
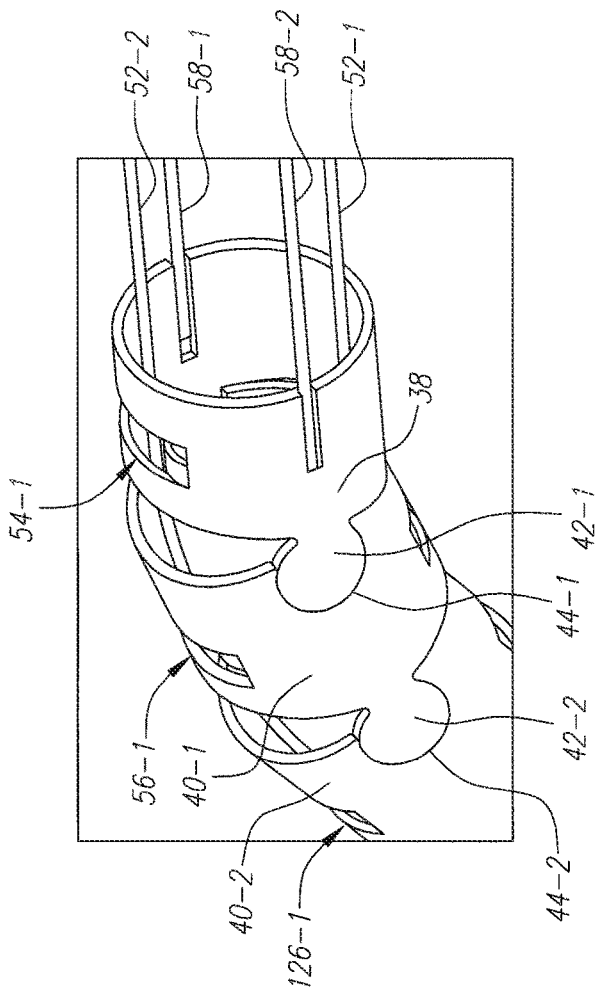
FIG. 5B is an isometric side and top view of the proximal side of the distal portion of the catheter shaft.

FIG. 5B is an isometric side and top view of the proximal side of the distal portion 18 of the catheter shaft 12. The first proximal pullwire 58-1 and the second proximal pull wire 58-2 can be attached to the proximal connector 38, as shown. In some embodiments, diametrically opposed longitudinal slots can be formed in a proximal end of the proximal connector 38 and the distal ends of the first and second proximal pullwires 58-1, 58-2 can be inserted in the longitudinal slots. In some embodiments, the distal ends of the first and second proximal pullwires 58-1, 58-2 can be welded to the proximal connector 38 and/or can be adhered to the proximal connector 38 with an adhesive.

The first and second distal pullwires 52-1, 52-2 can extend through the tabs 54-1, 56-1, 125-1, 126-1, 128-1 (and diametrically opposed corresponding tabs) to the distal tip 36, where a distal end of each pullwire is attached. As further depicted, the proximal connector 36 is connected to the pivoting hollow cylindrical segment 40-1 via the male connection 42-1 and the female connection 44-1. Additionally, a second pivoting hollow cylindrical segment 40-2 is connected to the pivoting hollow cylindrical segment 40-1 via the male connection 42-2 and the female connection 44-2.

FIG. 6A is a side view of a catheter shaft 12 in a first flexed state, in accordance with embodiments of the present disclosure. As depicted, the distal portion 18 is slightly deflected from an un-deflected state, shown in FIG. 1. In an example, tension can be applied to one of the first and second distal pullwires 52-1, 52-2 to deflect the distal portion 18. As the distal portion 18 is deflected, the proximal portion 16 can remain in an undeflected state and/or can be deflected in a direction that is different than the distal portion 18. For example, the distal portion 18 can be deflected in a direction of the arrow 28 along a first deflection plane, while the proximal portion 16 is deflected in a direction of arrow 27 along a second deflection plane. As discussed herein, the proximal portion 16 can include a proximal connective portion 15 and a distal connective portion 17.

FIG. 6B is a side view of the catheter shaft 12 in FIG. 5A in a second flexed state, in accordance with embodiments of the present disclosure. In an example, one of the first and second proximal pullwires 58-1, 58-2 can be tensioned, which can cause the proximal portion 16 to deflect along the arrow 27. As depicted in FIG. 6B, the proximal portion 16 can be deflected by a greater amount than that depicted in FIG. 6A. The greater deflection of the proximal portion 16 in FIG. 6B can be due to an increased tension being applied to one of the first and second proximal pullwires 58-1, 58-2. Because both of the first and second proximal pullwires 58-1, 58-2 can be connected to the proximal connector 38, the portion of the catheter shaft 12 located proximally to the proximal connector 38 (e.g., the proximal portion 16) can be deflected and a radius of curvature can be formed in the proximal portion 16. As discussed herein, because the proximal portion 16 and the distal portion 18 are decoupled from one another, a radius of curvature may not be introduced into the distal portion 18 when one of the first and second proximal pullwires 58-1, 58-2 are tensioned.

In some embodiments, a portion of the proximal portion 16 can be configured to deflect along a particular deflection plane. In an example, the distal connective portion 17 can include a planarity member and/or can be constructed of a different material than the proximal connective portion 15, which can enable the distal connective portion 17 to deflect along a particular deflection plane. For instance, the distal connective portion 17 can be actively deflected in a direction of arrow 27 by tensioning one of the first and second proximal pullwires 58-1, 58-2. The distal portion 18 can also be actively deflected in a direction of arrow 28 by tensioning one of the first and second distal pullwires 52-1, 52-2, as discussed herein. In some embodiments, a majority of the deflection of the proximal portion 16 can be confined to the distal connective portion 17 (e.g., a greater radius of curvature can be introduced into the distal connective portion 17 than in the proximal connective portion 15) through a particular construction of the distal connective portion 18, as discussed herein. In some embodiments, the catheter shaft 12 can include one or more portions such as the distal connective portion 17 that include a planarity member and/or can be constructed of a different material than the proximal connective portion 15, which can enable the one or more portions to deflect along a particular deflection plane (e.g., in a direction of arrow 18, arrow 27, or another direction).

In some embodiments, as one of the first and second distal pullwires 52-1, 52-2 are tensioned, the distal portion 18 can be deflected and a radius of curvature can be formed in the distal portion 18. As previously discussed, because the distal portion 18 and the proximal portion 16 are decoupled from one another, a radius of curvature may not be introduced into the proximal portion 16 when one of the first and second distal pullwires 52-1, 52-2 are tensioned. In some embodiments, and as depicted in FIG. 6B, one of the first and second distal pullwires 52-1, 52-2 can be tensioned and one of the first and second proximal pullwires 58-1, 58-2 can be tensioned to introduce a radius of curvature into the distal portion 18 and into the proximal portion 16. In an example, the proximal portion 16 can be deflected in a direction of arrow 27 and the distal portion 18 can be deflected in a direction of arrow 28. As such, the proximal portion 16 and the distal portion 18 can be deflected along different planes and a different radius of curvature can be introduced into the proximal portion 16 and the distal portion 18.

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment of a deflectable catheter shaft has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter shaft, comprising:
   an elongated structure that includes a distal portion and a proximal portion, wherein the distal portion includes a distal tip, a proximal connector, and a plurality of pivoting hollow cylindrical segments disposed between the proximal connector and the distal tip along a longitudinal axis that extends through the elongated structure;
   a plurality of connections disposed along diametrically opposed sides of the distal portion that are configured to connect the distal tip, the plurality of pivoting hollow cylindrical segments, and the proximal connector;
   a diametrically opposed pair of tabs that extend from an inner wall of each of the plurality of pivoting hollow cylindrical segments that forms a first and second pullwire tunnel; and
   a first and second pullwire that extend through the first and second pullwire tunnel.

2. The catheter shaft of claim 1, wherein the diametrically opposed pair of tabs are 90 degrees opposed to the connections.

3. The catheter shaft of claim 1, wherein the diametrically opposed pair of tabs are defined by cross-longitudinal cuts made in a wall of each of the hollow cylindrical segments.

4. The catheter shaft of claim 3, wherein the cross-longitudinal cuts are perpendicular to a longitudinal axis of each of the hollow cylindrical segments.

5. The catheter shaft of claim 3, wherein the cross-longitudinal cuts are between parallel and perpendicular to a longitudinal axis of each of the hollow cylindrical segments.

6. The catheter shaft of claim 1, wherein the distal portion of the catheter shaft is configured to deflect perpendicular to a plane that extends through the plurality of connections when tension is applied to at least one of the first and second pullwires.

7. The catheter shaft of claim 6, wherein each of the plurality of connections includes a male and female connection configured to allow each of the plurality of pivoting hollow cylindrical segments to deflect bi-directionally.

8. The catheter shaft of claim 7, wherein the male connection is a longitudinally extending projection and the female connection is a socket corresponding to the longitudinally extending projection.

9. The catheter shaft of claim 6, wherein:
   the distal portion is formed from a unitary piece of material; and
   diametrically opposed pivot spaces are formed between the distal tip, each of the plurality of pivoting hollow cylindrical segments, and the proximal connector that define the plurality of connections.

10. A catheter shaft, comprising:
    an elongated structure, wherein the elongated structure includes a distal portion and a proximal portion;
    the distal portion including a proximal hollow cylindrical segment disposed next to and connected with a pivoting hollow cylindrical segment, the proximal hollow cylindrical segment including a distal face and the pivoting hollow cylindrical segment including a proximal face;

a first and second longitudinally extending projection disposed on at least a first one of the distal face of the proximal hollow cylindrical segment and the proximal face of the pivoting hollow cylindrical segment;

a first and second socket corresponding to the first and second longitudinally extending projections disposed on at least a second one of the distal face of the proximal hollow cylindrical segment and the proximal face of the pivoting hollow cylindrical segment; and a diametrically opposed pair of tabs that extend from an inner wall of each hollow cylindrical segment, wherein the diametrically opposed pair of tabs define a first and second pullwire tunnel.

11. The catheter shaft of claim 10, wherein:

the diametrically opposed pair of tabs are 90 degrees opposed to the longitudinally extending projections and the sockets; and the tabs are configured to accept a pullwire that passes from the proximal portion to the distal portion.

12. The catheter shaft of claim 10, wherein:

each tab is defined by cross-longitudinal cuts made in a wall of each of the hollow cylindrical segments; and each tab includes a proximal finger and distal finger adjacently opposed to one another.

13. The catheter shaft of claim 12, wherein the cross-longitudinal cuts are perpendicular to a longitudinal axis of each of the hollow cylindrical segments.

14. The catheter shaft of claim 10, wherein:

the hollow cylindrical segments are formed from a rigid material; and the longitudinally extending projections and the corresponding sockets are formed via laser cutting the rigid material.

15. The catheter shaft of claim 10, wherein the proximal hollow cylindrical segment is attached to the proximal portion at a proximal end of the proximal hollow cylindrical segment.

16. The catheter shaft of claim 10, wherein an ultrasound transducer is connected to the distal end of the distal hollow cylindrical segment.

17. The catheter shaft of claim 10, wherein:

the distal portion includes the proximal hollow cylindrical segment and a distal hollow cylindrical segment connected via a plurality of pivoting hollow cylindrical segments;

a pair of diametrically opposed pullwires passes from the proximal portion, through the diametrically opposed pairs of tabs and is connected to the distal hollow cylindrical segment.

18. The catheter shaft of claim 17, wherein the distal portion is configured for bi-directional deflection along a plane that extends through each of the pullwires.

19. A catheter shaft, comprising:

an elongated structure, wherein the elongated structure includes a distal portion that includes a distal tip and a proximal portion connected to the distal portion;

the distal portion including a plurality of hollow cylindrical segments that are connected to one another via diametrically opposed hinges, wherein each of the plurality of hollow cylindrical segments includes a diametrically opposed pair of tabs that extend from an inner wall of each hollow cylindrical segment to form first and second diametrically opposed pullwire tunnels;

a first pullwire that extends from the proximal portion through the first pullwire tunnel and is connected to the distal tip, wherein pulling of the first pullwire causes the distal tip to deflect in a first direction; and a second pullwire that extends from the proximal portion through the second pullwire tunnel and is connected to the distal tip, wherein pulling of the second pullwire causes the distal tip to deflect in a second direction.

20. The catheter shaft of claim 19, wherein:

each tab is formed by at least one cross-longitudinal cut made in a wall of each of the plurality of hollow cylindrical segments; and each tab is folded inwardly toward a central longitudinal axis passing through the distal portion of the catheter shaft.

21. The catheter shaft of claim 20, wherein the diametrically opposed pair of tabs are 90 degrees opposed to the diametrically opposed hinges.

22. The catheter shaft of claim 20, wherein the distal portion is formed from a unitary piece of material.

23. The catheter shaft of claim 20, wherein the distal portion includes diametrically opposed pivot spaces between each of the hollow cylindrical segments configured to allow for bi-directional deflection of each of the hollow cylindrical segments about the diametrically opposed hinges.

* * * * *